United States Patent
Barnes

(10) Patent No.: US 11,587,671 B2
(45) Date of Patent: Feb. 21, 2023

(54) AUTOMATIC ASSOCIATION OF MEDICAL ELEMENTS

(71) Applicant: CareFusion 303, Inc., San Diego, CA (US)

(72) Inventor: Erik Barnes, Solana Beach, CA (US)

(73) Assignee: CareFusion 303, Inc., San Diego, CA (US)

(*) Notice: Subject to any disclaimer, the term of this patent is extended or adjusted under 35 U.S.C. 154(b) by 0 days.

(21) Appl. No.: 17/503,211

(22) Filed: Oct. 15, 2021

(65) Prior Publication Data

US 2022/0037008 A1 Feb. 3, 2022

Related U.S. Application Data

(63) Continuation of application No. 16/984,000, filed on Aug. 3, 2020, now Pat. No. 11,152,113, which is a
(Continued)

(51) Int. Cl.
*G16H 40/40* (2018.01)
*G06F 16/23* (2019.01)
(Continued)

(52) U.S. Cl.
CPC ............ *G16H 40/40* (2018.01); *G06F 16/23* (2019.01); *G06Q 10/06* (2013.01); *G06Q 50/22* (2013.01);
(Continued)

(58) Field of Classification Search
CPC ........ G16H 40/40; G16H 10/60; G16H 20/10; G06F 16/23; G06F 19/322; G06F 19/327;
(Continued)

(56) References Cited

U.S. PATENT DOCUMENTS 7,962,544 B2 * 6/2011 Torok .................. H04L 67/12
709/200
8,360,975 B1 1/2013 Schwieterman et al.
(Continued)

FOREIGN PATENT DOCUMENTS

JP 2005-199064 A 7/2005

OTHER PUBLICATIONS

European Summons to attend oral proceedings pursuant to Rule 115(1) EPC for Application No. 11827387.9, dated Jan. 18, 2019, 7 pages.
(Continued)

*Primary Examiner* — Andrew W Bee
(74) *Attorney, Agent, or Firm* — Morgan, Lewis & Bockius LLP

(57) ABSTRACT

An infusion system automatically determines when an infusion device moved within a physical area associated with a patient, and automatically displays an electronic list of procedures or prescriptions associated with the patient based on determining the infusion device moved within the physical area associated with the patient and receiving the indication of the operation. When a selection is received from the electronic list, operating parameters associated with the selection and the patient are automatically downloaded from a remote computing device to the infusion device.

20 Claims, 8 Drawing Sheets

Related U.S. Application Data continuation of application No. 16/506,914, filed on Jul. 9, 2019, now Pat. No. 10,755,807, which is a continuation of application No. 15/934,867, filed on Mar. 23, 2018, now Pat. No. 10,347,375, which is a continuation of application No. 14/337,151, filed on Jul. 21, 2014, now Pat. No. 9,946,837, which is a continuation of application No. 12/890,447, filed on Sep. 24, 2010, now Pat. No. 8,786,402.

(51) Int. Cl.
  G06Q 10/06 (2023.01)
  G06Q 50/22 (2018.01)
  G16H 10/60 (2018.01)
  G16H 20/10 (2018.01)
  *G06Q 10/10* (2023.01)

(52) U.S. Cl.
  CPC ............ G16H 10/60 (2018.01); G16H 20/10 (2018.01); *G06Q 10/10* (2013.01)

(58) Field of Classification Search
  CPC ............ G06F 19/3406; G06F 19/3456; G06F 19/3462; G06Q 10/06; G06Q 50/22; A61B 5/1113
  See application file for complete search history.

(56) References Cited

U.S. PATENT DOCUMENTS

| | | | |
|---|---|---|---|
| 8,775,196 | B2 | 7/2014 | Simpson et al. |
| 9,250,104 | B2 | 2/2016 | Greiner |
| 2002/0044059 | A1 | 4/2002 | Reeder et al. |
| 2004/0019464 | A1 | 1/2004 | Martucci et al. |
| 2004/0073453 | A1 | 4/2004 | Nenov et al. |
| 2004/0176667 | A1* | 9/2004 | Mihai ............... G16H 40/67 600/300 |
| 2005/0055242 | A1 | 3/2005 | Bello |
| 2005/0055244 | A1 | 3/2005 | Mullan et al. |
| 2005/0065817 | A1 | 3/2005 | Mihai et al. |
| 2005/0097595 | A1 | 5/2005 | Lipsanen et al. |
| 2005/0234381 | A1 | 10/2005 | Niemetz et al. |
| 2006/0200369 | A1 | 9/2006 | Batch et al. |
| 2007/0299317 | A1 | 12/2007 | Hoyme et al. |
| 2008/0082362 | A1 | 4/2008 | Haider |
| 2008/0126126 | A1 | 5/2008 | Ballai |
| 2008/0189783 | A1 | 8/2008 | Music et al. |
| 2009/0119124 | A1 | 5/2009 | Kambaloor |
| 2010/0001838 | A1 | 1/2010 | Miodownik et al. |
| 2010/0179819 | A1 | 7/2010 | Herbst |
| 2010/0199015 | A1 | 8/2010 | Martucci et al. |
| 2010/0292556 | A1 | 11/2010 | Golden |
| 2011/0054936 | A1 | 3/2011 | Cowan et al. |
| 2011/0077965 | A1* | 3/2011 | Nolte ............... G06Q 10/10 705/2 |
| 2011/0305376 | A1 | 12/2011 | Neff |

OTHER PUBLICATIONS

Australian Patent Examination Report No. 1 for Application No. 2011305586, dated Feb. 26, 2016, 7 pages.
European Office Action for Application No. 11827387.9, dated Sep. 23, 2016, 5 pages.
Canadian Office Action for Application No. 2810924, dated Jun. 8, 2017, 3 pages.
International Preliminary Report on Patentability for Application No. PCT/US2011/052422, dated Apr. 23, 2012, 6 pages.
Australian Examination Report No. 1 for Application No. 2017201295, dated Feb. 26, 2018, 7 pages.
Australian Office Action for Application No. 2019203878, dated Jun. 17, 2020, 4 pages.
European Decision to refuse a European Patent Application for Application No. 11827387.9, dated Jul. 4, 2019, 35 pages.
Australian Office Action for Application No. 2019203878, dated Mar. 22, 2021, 5 pages.
Australian Office Action for Application No. 2021204015, dated Aug. 24, 2022, 3 pages.

\* cited by examiner

AUTOMATIC ASSOCIATION OF MEDICAL ELEMENTS

CROSS-REFERENCE TO RELATED APPLICATIONS

The present application is a continuation of U.S. application Ser. No. 16/984,000, entitled "AUTOMATIC ASSOCIATION OF MEDICAL ELEMENTS," filed on Aug. 3, 2020, now U.S. Pat. No. 11,152,113, which is a continuation application of U.S. application Ser. No. 16/506,914, entitled "AUTOMATIC ASSOCIATION OF MEDICAL ELEMENTS," filed on Jul. 9, 2019, now U.S. Pat. No. 10,755,807, which is a continuation application of U.S. application Ser. No. 15/934,867, entitled "AUTOMATIC ASSOCIATION OF MEDICAL ELEMENTS," filed on Mar. 23, 2018, now U.S. Pat. No. 10,347,375, which is a continuation application of U.S. application Ser. No. 14/337,151, entitled "AUTOMATIC ASSOCIATION OF MEDICAL ELEMENTS," filed on Jul. 21, 2014, now U.S. Pat. No. 9,946,837, which is a continuation of U.S. application Ser. No. 12/890,447, entitled "AUTOMATIC ASSOCIATION OF MEDICAL ELEMENTS," filed on Sep. 24, 2010, now U.S. Pat. No. 8,786,402, the entirety of each of which is incorporated herein by reference.

BACKGROUND

The present disclosure generally relates to systems and methods of identifying the location of people and equipment, and, in particular, relates to the automatic association of medical equipment with proximate caregivers and patients.

DESCRIPTION OF THE RELATED ART

A commonly followed procedure to ensure the safety of patients being treated in hospitals has been the establishment of the "five rights" of medication administration. These are (1) right patient, (2) right time, (3) right medication, (4) right route of administration, and (5) right dose. For a medication administered via an intravenous (IV) pump, for example, it requires care and attention by the nurse or other caregiver to ensure that the medication matches the patient and that it is administered at the proper flow rate and the proper time. Patients also may receive treatment involving a medical substance other than a medication, e.g. a "normal saline" solution (9 grams of sodium chloride (NaCl) dissolved in 1 liter of water) administered as an infusion to treat dehydration. Maintaining the required level of attention to ensure that medications and medical substances are properly administered can be a challenge in the hectic environment of a hospital.

Automated processes have been increasingly implemented to reduce the potential for human error. Scanning a barcode that is printed on a wristband worn by a patient, for example, ensures that the patient is correctly identified. This type of process, however, often carries a penalty of increased complexity of the process wherein the nurse must manually scan one or more barcodes, which also increases the amount of time required for the nurse to complete a procedure.

SUMMARY

In order to improve the safety of the patient while simultaneously eliminating at least some of the time-consuming steps of manually scanning barcodes to identify one or more of the patient, the caregiver, the medication, or the medical device, it is advantageous to provide an automatic association of a patient with the medical device and a medication or other medical substance that are physically proximate to them. Furthermore, the nurse who is also proximate to the patient can be identified and associated with the medical device both for determining the allowable privileges in configuring the medical device and in recording the administration of a medication. The combination of associating a medical device with a patient, a medication with the patient and with the medical device, and the caregiver with all of these elements provides an automatic way to verify the five rights of medication administration.

The disclosed method and system provides for the automatic association of elements that are in or enter a single defined physical space. These elements include one or more of a patient, a medical device, a medication or medical substance, and a caregiver. The association of these elements enables the automatic configuration of the medical device to administer the medication to the patient as well as providing an automatic record of the caregiver and the details of the administration of the medication or medical substance.

A method of associating a plurality of objects is disclosed, wherein the method comprises the steps of defining a physical space, determining by use of a real time locating system (RTLS) what objects are within the physical space, and associating the objects determined by the RTLS to be within the physical space, wherein the objects include at least one of a caregiver, a patient, a medical device, a medication, and a medical substance.

A method of associating a plurality of objects is disclosed, wherein the method comprises the steps of defining a physical space about a first device, determining by use of a RTLS objects that are within the physical space, and associating the objects within the physical space with the first device, wherein the objects include at least one of an operator, a user, a second device, and a supply.

A system is disclosed that includes a RTLS transceiver coupled to a processor. The RTLS transceiver is configured to identify and locate one or more objects having a RTLS tag and provide information comprising the identification and location of the tagged objects. The processor is configured to define a physical space, receive the identification and location of the tagged objects, and associate objects that are within the physical space.

A computer-readable medium having computer-executable instructions stored thereon for execution by a processor to perform a method of associating a plurality of objects is disclosed, wherein the method comprises defining a physical space about a first device, determining by use of a RTLS what objects are within the physical space, and associating the objects within the physical space with the first device, wherein the objects include at least one of an operator, a user, a second device, and a supply.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed methods and system provide for the automatic association of elements that are determined to be within a defined physical space. These elements include one or more of a patient, a medical device, a medication or medical substance, and any nurse, doctor, or other caregiver. Once these items are associated, one or more of the elements may be configured according to the association with other elements, privileges may be granted based on the identification of the caregiver present in the physical area, and records kept of actions and events that occur wherein the records include the dedication of the patient, the medical equipment, the medication or medical substance, and the identities of the caregiver or caregivers that are present in the defined physical area.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The method and system disclosed herein are presented in terms of the administration of a medication as an IV fluid using an IV pump to a patient in a hospital. The method and system, however, are equally applicable to other medical settings such as an outpatient clinic and to nonmedical applications where it is desirable to associate various elements based on a common presence within a defined physical space. Nothing in this disclosure should be interpreted, unless specifically stated as such, to limit the application of any method or system disclosed herein to a medical or hospital environment.

Figure 1:
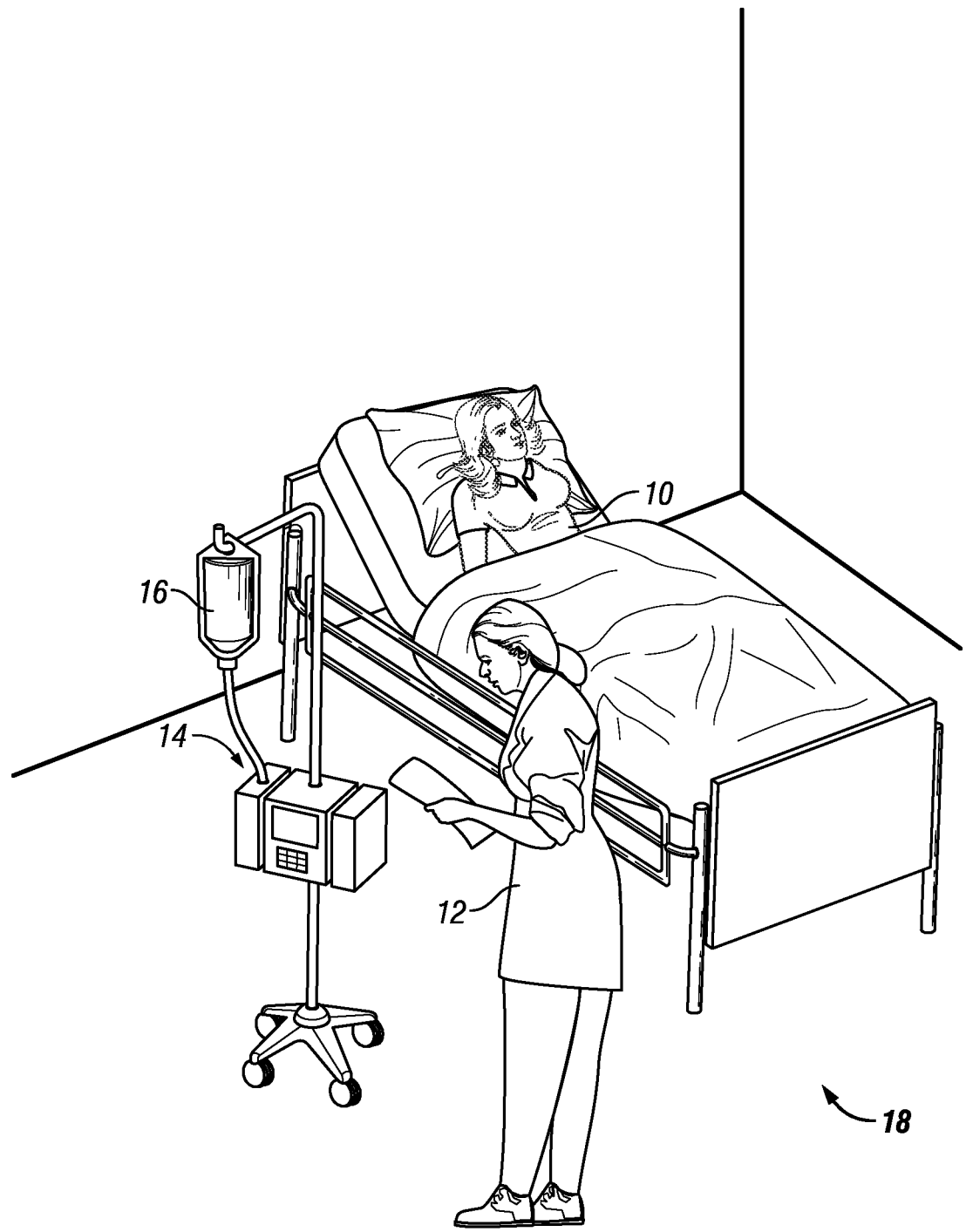
FIG. 1 depicts an example hospital room where a patient is to receive treatment according to certain aspects of this disclosure.

FIG. 1 depicts an example hospital room 18 where a patient 10 is to receive treatment according to certain aspects of this disclosure. In this example, a patient 10 is to receive an infusion of a medication 16 using an IV pump 14, wherein this medication 16 is to be administered by a nurse 12. To ensure the safety of the patient, the nurse 12 must verify that medication 16 has been prescribed for patient 10, ensure that IV pump 14 is configured to deliver the medication 16 at the prescribed rate, and record all of the details of this medication administration in the patient's medication administration record (MAR). Performing these tasks takes time and careful attention and there is always the risk, even with the most conscientious personnel, of making a mistake or forgetting to record something in these manual processes.

Figure 2:
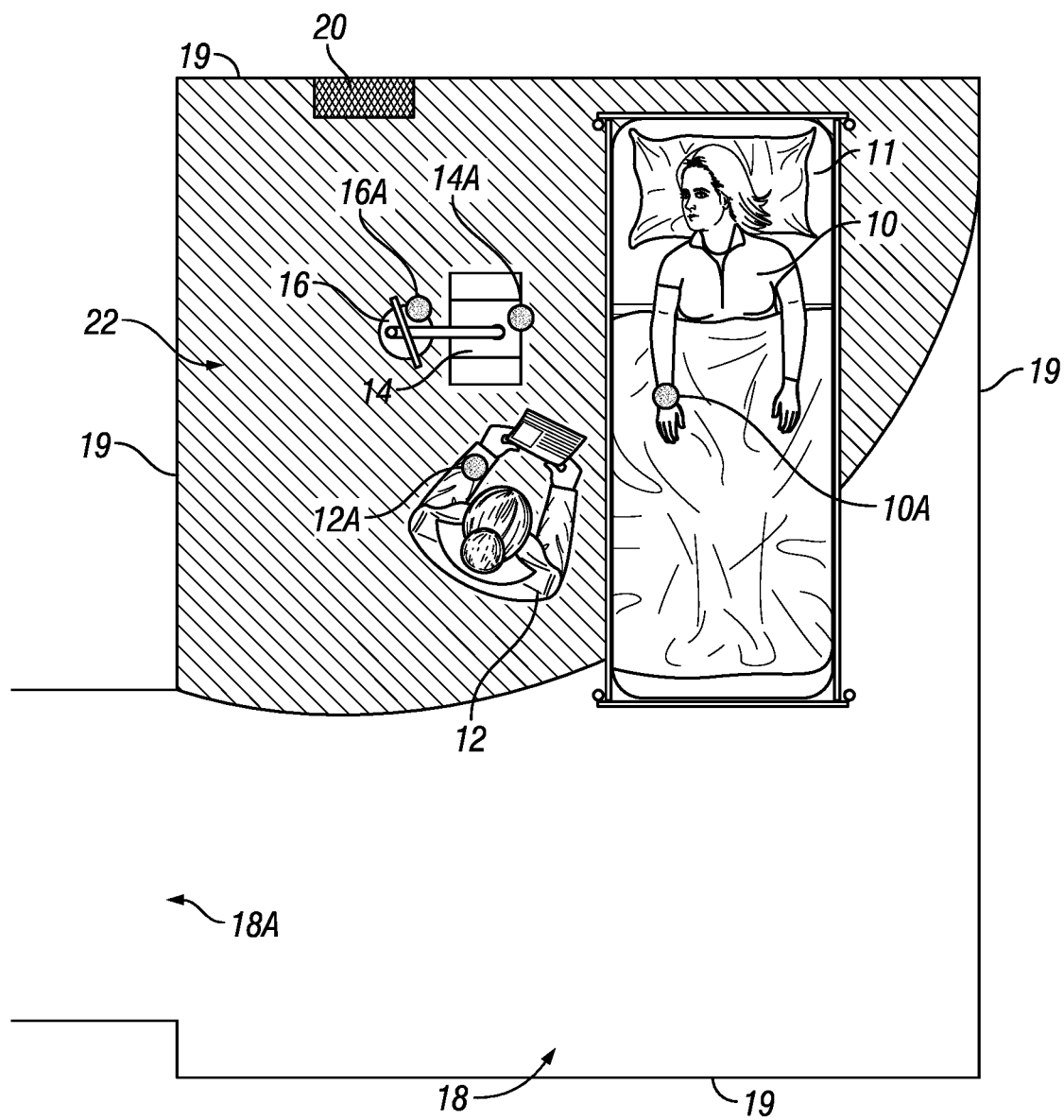
FIG. 2 is a plan view of the room of FIG. 1 showing the coverage of an example RTLS system according to certain aspects of this disclosure.

FIG. 2 is a plan view of the room of FIG. 1 showing the coverage of an example RTLS system according to certain aspects of this disclosure. A RTLS identifies objects and tracks the location of the objects in real time using "tags" that are attached to or embedded in the objects. The tags comprise wireless transmitters and the RTLS comprises at least one transceiver that comprises at least one antenna to receive the wireless signals from the tags. The transceivers are connected to a central controller, e.g. a part of the RTLS system 44 of FIG. 6, over, in some cases, a standard communication network such as a wired or wireless Ethernet network 50. The central controller comprises a processor that controls the function of the transceivers and stores, e.g. in database 44 of FIG. 6, the locations of all objects that have RTLS tags and are within the range of at least one transceiver. In some cases, the transceivers communicate wirelessly between each other to form a mesh network that links to the central controller. The range of the antenna of each transceiver defines a physical space, e.g. the physical space 22 of FIG. 2, such that an object is known to be within the physical space when the transceiver are able to receive the wireless signal transmitted by the tag that is attached to the object. In some RTLS systems, the location of the object within the space can be further determined using the signal strength measured by the transceiver or, if the physical spaces associated with multiple transceivers overlap, receipt of the tag's signal by multiple transceivers. RTLSs may be purchased from companies such as the Awarepoint Corp. of San Diego, Calif., USA and Centrak of Newtown, Pa., USA.

RTLS tags may be generic, wherein all objects of a certain type have tags that are indistinguishable from each other, or specific, wherein each tag has a unique identifier that is part of the wireless signal broadcast by the tag. For example, a tag that is attached to an IV pump 14 may be programmed to either broadcast a code associated with all IV pumps (generic) or broadcast the serial number of that IV pump 14 (specific). Similarly, a tag that is embedded in the identification (ID) badge of a nurse 12 may broadcast the ID number assigned to that nurse 12 (specific). A tag that is attached to a medicine, for example, such as an IV bag 16 containing a custom mixture of medications may broadcast the unique serial number of that specific IV bag 16 (specific). Some tags broadcast a unique identifier that is associated with the tag, wherein the tag identifier is associated in the database 48 with the object to which the tag is attached, the association of the tag identifier with the object being made when the tag was attached to the object. It will be apparent to those of ordinary skill in the art that a RTLS tag may be associated with the object to which the tag is attached in many other ways.

RTLS tags typically broadcast their signal at intervals that may range from a few seconds to a few minutes. When a tag first enters a physical space and the signal broadcast by the tag is detected by the transceiver associated with that space, the presence of the object associated with that tag in that physical space is recorded in the database. When a tag is no longer detected by the receiver associated with the physical space in which it was previously detected, or when the tag is detected to be in a new physical space, the location information stored in the database is updated. Thus, the location of all objects that carry RTLS tags are known on a near-real-time basis, wherein the latency, i.e. the delay between a change in location and the change being recorded in the database, is determined in part by the time interval between broadcasts by the RTLS tags.

In the example of FIG. 2, a RTLS transceiver 20 is mounted on a wall 19 of a patient room 18, wherein the RTLS transceiver 20 has a range that defines a physical space 22 (shown as the shaded region in FIG. 2) wherein the RTLS transceiver 20 is able to communicate with RTLS tags. The physical space covers a portion of the room 18 that includes the patient bed 11. The range of the RTLS transceiver 20 is such that, in this example, it does not extend out the door 18A. The patient 10, currently lying in bed 11, is wearing a RTLS tag 10A that is, in this example, part of his patient identification wristband. The nurse 12 is wearing a RTLS tag 12A as part of her ID badge. The IV pump 14 has a RTLS tag 14A attached to it. The IV bag of medication 16 also has a RTLS tag 16A attached to it. All of the tags 10A, 12A, 14A, and 16A are within the defined physical space 22 in FIG. 2.

Multiple associations can be made of objects within the defined physical space 22. In this example, the patient was alone in the room 18 prior to the arrival of the nurse 12 with the IV pump 14 and the medication 16. The defined physical space 22 was therefore first associated with patient 10. When the nurse 12 arrived with the IV pump 14 and medication 16, the IV pump 14 was associated with patient 10, the medication 16 was associated with both the patient 10 and the IV pump 14, and the nurse 12 was associated with the IV pump 14 to enable the IV pump 14 to be configured according to the privileges assigned to nurse 12.

When an IV pump 14 has been associated with a patient 10, additional safeguards and automatic actions become possible. For example, if the patient 10 who is associated with the IV pump 14 becomes separated from the IV pump 14, the nurse 12 assigned to the patient 10 can be notified to immediately check on the patient 10. Similarly, if a change in one of the operating parameters of the IV pump 14 occurs when no caregiver is proximate to the IV pump 14, the nurse 12 assigned to the patient 10 can be notified to immediately check on the settings of the IV pump 14.

The detection and identification of all of the caregivers that are within the defined physical space 22 when an action occurs allows certain actions to be taken without first requiring the caregiver to log onto the medical device 14. For example, conventional medical devices sometimes require the caregiver to type in their password or otherwise identify themselves prior to the caregiver being able to silence an alarm. This is both time-consuming, at a time when the caregiver is focused on correcting a condition for which the alarm sounded, and stressful, as it may be difficult to correctly type a password while an alarm is sounding at close range. The disclosed system overcomes these difficulties by enabling the alarm to be canceled when a caregiver 12 is within the same defined physical space 22 as the medical device 14. In certain embodiments, the caregiver 12 can walk into a room 18 and, as the caregiver 12 will be associated with the medical device 14 by the time the caregiver 12 reaches the medical device 14, the caregiver 12 may simply press the button on the medical device 14 to deactivate the alarm without any preliminary action.

Figure 3A:
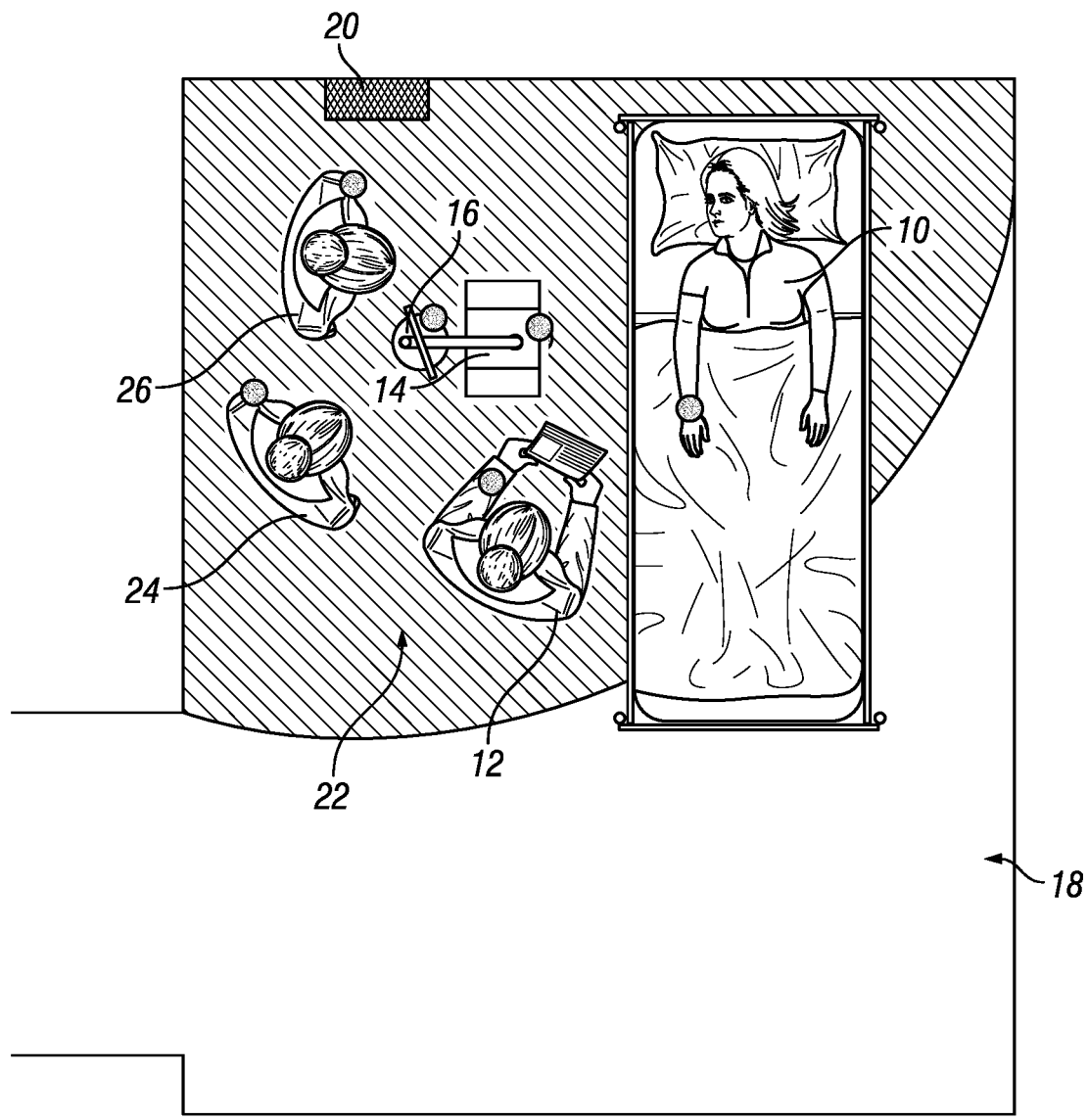
FIG. 3A is a plan view similar to FIG. 2 where multiple caregivers are present within the defined physical space according to certain aspects of the disclosure.

FIG. 3A is a plan view similar to FIG. 2 where multiple caregivers are present within the defined physical space according to certain aspects of the disclosure. In this example, the patient 10 and nurse 12 have been joined in room 18 by doctors 24 and 26. The nurse 12 and doctors 24,26 are all standing within the defined physical space 22. In this example, the doctors 24,26 have been assigned privileges related to the IV pump 14 that are greater than the privileges assigned to nurse 12. For example, the doctors 24,26 may be assigned the privilege of setting the flow rate outside of the standard boundaries defined in the hospital protocols, while the nurse 12 may only set the flow rate to a value within the standard boundaries. In this example, the IV pump 14 has been enabled to accept operating parameters according to the highest privileges of the three caregivers 12,24,26 who are within the defined physical space 22. A record will be created that includes the identification of all caregivers 12,24,26 who are within the defined physical space 22 at the time the operating parameters were adjusted or other events occur. Although the identities of the caregivers 12,24,26 are recorded by the disclosed system, it is not recorded by the system which of the caregivers 12,24,26 took the action. What is noted is the presence of the caregivers 12,24,26 in the defined space 22 when the action was taken. In certain embodiments, a caregiver 12 must log into the IV pump 14 before the IV pump 14 will accept operating parameters, and then will accept operating parameters according to the privileges of the logged-in caregiver 12. The record will include the identification of at least the logged-in caregiver 12. In certain other embodiments, a caregiver 12 must simply identify themselves from a list of the caregivers 12,24,26 that are currently within the defined space 22.

Figure 3B:
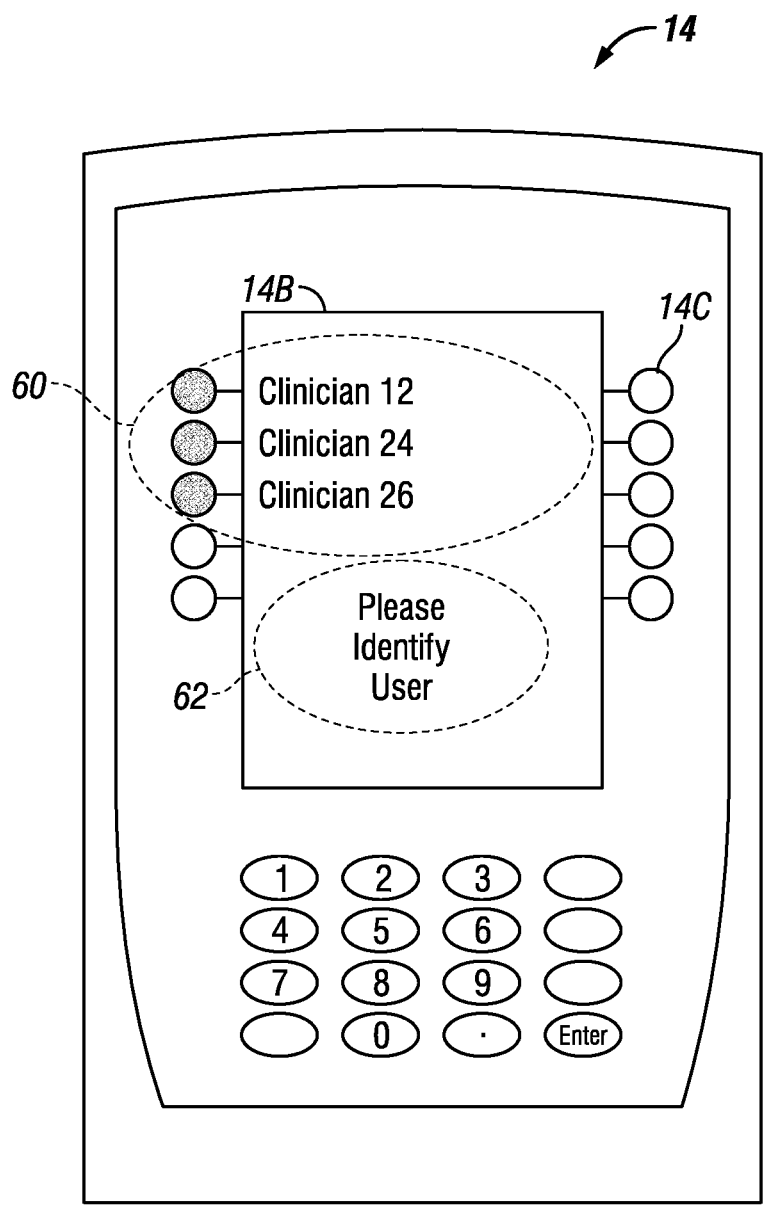
FIG. 3B is an exemplary display of an IV pump requesting selection of one of the multiple caregivers present in FIG. 3B according to certain aspects of the disclosure.

FIG. 3B is an exemplary display of an IV pump 14 requesting selection of one of the multiple caregivers 12,24, 26 present in FIG. 3B according to certain aspects of the disclosure. The IV pump is coupled, in this example, through a wired or wireless communication link, e.g. communication link 52 of FIG. 6, to a server 46 (not shown in FIG. 3B) that is coupled to the RTLS system 44 (not shown in FIG. 3B) as discussed in more detail in FIG. 6. In this example, it is necessary to identify a specific clinician who has taken an action for the purpose of record-keeping. To this end, a message is sent from the server 46 to the IV pump 14 containing the identification of the caregivers 12,24,26 who have been detected to be within the physical space 22. The example IV pump 14 shown in FIG. 3B comprises a graphic display 14B and a series of buttons 14C on each side of the display 14B. A list of the three clinicians 12,24,26 is presented on the display 14B, as shown within the broken-line oval 60. The display 14B also presents an instructional message as shown within the broken-line oval 62. The clinician to be identified is selected by pressing the button 14C that is next to their name. This selection is transmitted back to the server 46 and stored in the database 48. In certain embodiments, the server verifies that the patient has a prescription comprising the medication; and downloads configuration information to the medical device according to the prescription. In certain embodiments, a list of medications is presented when more than one medication 16 is determined to be within the defined physical space 22. In certain embodiments, a list of procedures or prescriptions is presented when more than one prescription has been found in the database associated with medication 16 and patient 10 and not already associated with a device. In certain embodiments, operating parameters that are associated with a procedure that has been ordered for the patient are downloaded from the database. In certain embodiments, data records that are associated with a procedure that has been performed for the patient are uploaded from the medical device to the database.

Figure 4:
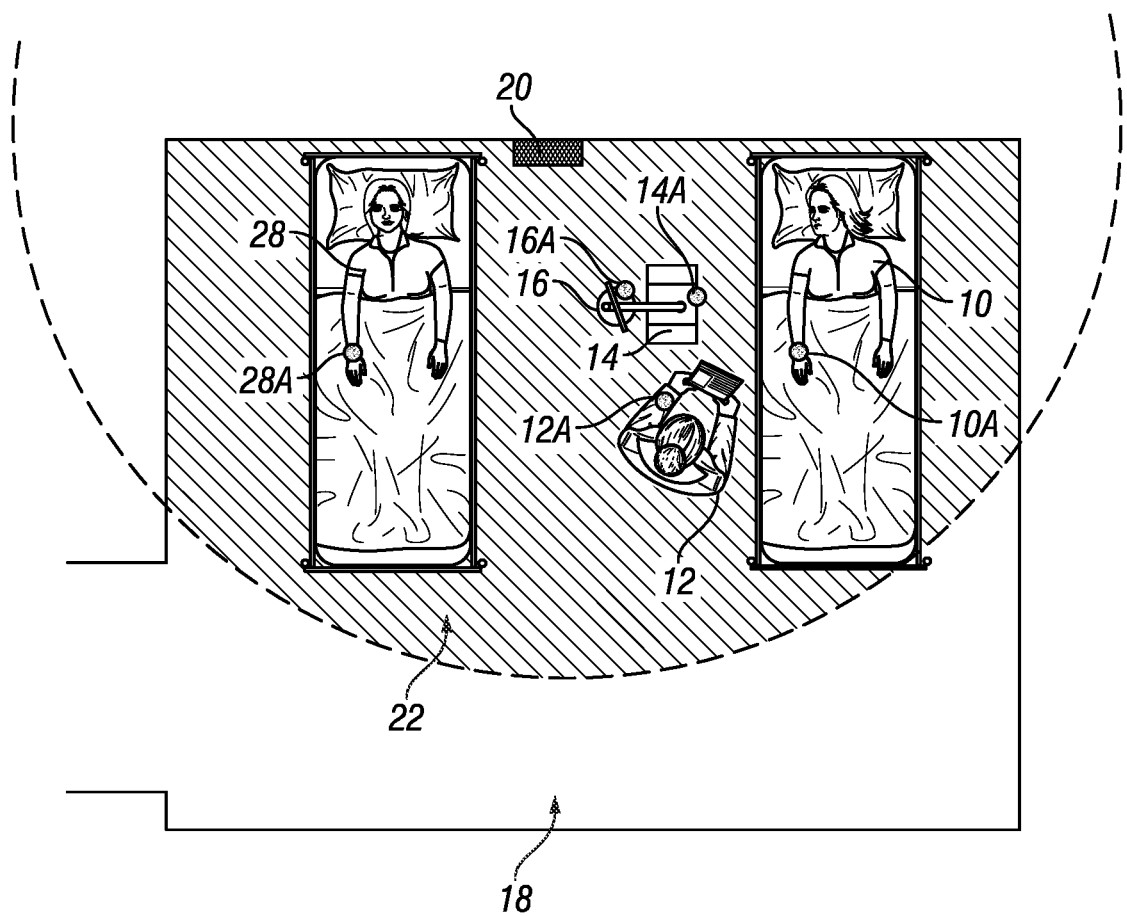
FIG. 4 depicts a plan view of a room in which multiple patients are present within the defined physical space according to certain aspects of the disclosure.

FIG. 4 depicts an example wherein multiple patients 10 and 28 are present within the defined physical space 22 according to certain aspects of the disclosure. In this example, hospital room 18 is shared by two patients 10 and 28 who are wearing RTLS tags 10A and 28A, respectively. Similar to the example of FIGS. 1 and 2, nurse 12 is preparing to administer medication 16 to patient 10 using IV pump 14. Both patient 10 and patient 28 and their RTLS tags 10A and 28A, however, are within the defined physical space 22. It is not possible to determine solely from their presence within defined physical space 22 which patient is to receive the medication 16. In this example, however, there is a prescription for the administration of medication 16 to patient 10 while there is no such prescription for administration of medication 16 to patient 28. Medication 16 has therefore been associated with patient 10. This association is presented on the display of IV pump 14 for verification by the nurse 12. In certain embodiments, the nurse 12 is presented with a display on IV pump 14 of the names of the two patients 10 and 28, similar to the presentation of the names of the multiple clinicians 12,24,26 on the IV pump 14 in FIG. 3B, and the nurse 12 chooses the name of the patient 10 who will receive the medication 16. It is faster and less susceptible to error to select from a short list of patients rather than search the entire roster of patients in the hospital. In certain embodiments, the patient 10 remains associated with IV pump 14 until the IV pump 14 is reassigned or another specified event occurs, such as a discharge of the patient, that has been defined to break the association of the IV pump 14 and the patient 10.

Figure 5:
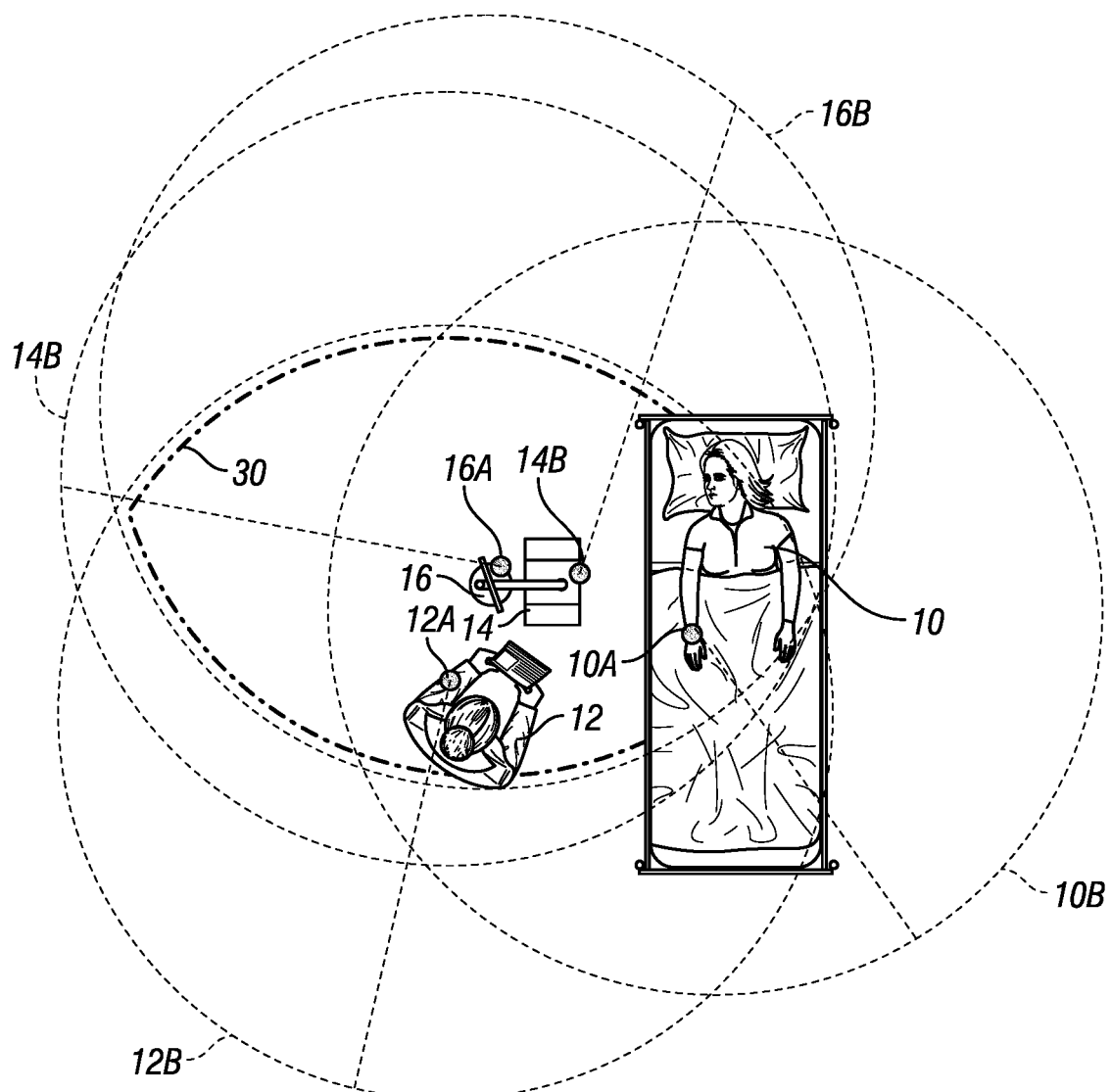
FIG. 5 depicts an embodiment wherein the proximity of the elements to be associated is based on interaction of the individual RTLS tags according to certain aspects of the disclosure.

FIG. 5 depicts an embodiment wherein the proximity of the elements to be associated is based on interaction of the individual RTLS tags according to certain aspects of the disclosure. In this example, the RTLS tags interact among themselves to determine what elements are within close proximity of each other. Each tag has a limited range. For example, the RTLS tag 10A worn by patient 10 has a range indicated by the broken line circle 10B. Similarly, RTLS tag 12A worn by nurse 12 has a range 12B, RTLS tag 14A on IV pump 14 has a range of 14B, and RTLS tag 16A attached to medication 16 has a range 16B. It can be seen that these four ranges overlap within the area 30 indicated by the thicker dot-dash line. Associations are made between elements within this common area 30 enabling certain actions, such as IV pump 14 retrieving the privileges of nurse 12 based solely on their proximity and prior to any action by nurse 12. Similarly, the proximity of medication 16 and patient 10 triggers the retrieval of any prescription for patient 10 that includes the administration of medication 16.

Figure 6:
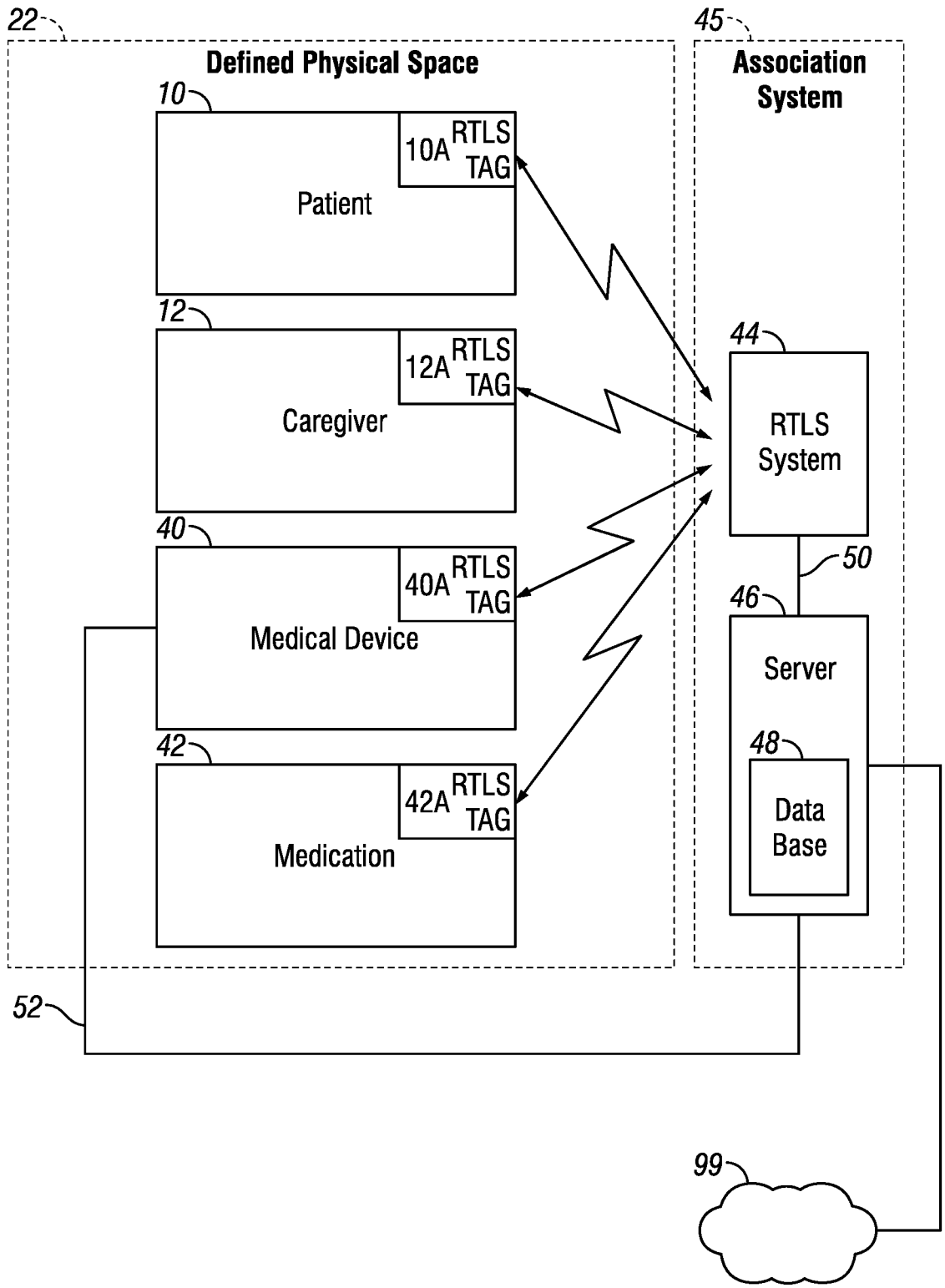
FIG. 6 is a block diagram of an example configuration of the RTLS and the elements to be associated according to certain aspects of the disclosure.

FIG. 6 is a block diagram of an example configuration of the RTLS and the elements to be associated according to certain aspects of the disclosure. In this example, an association system 45 has been created comprising a RTLS system 44 and a server 46. The server 46 includes a database 48 that contains information about medications prescribed for patients in the hospital, the privileges of the staff within the hospital, and operating parameters for medical devices within the hospital. In this example, the defined physical space 22 contains one patient 10 wearing a RTLS tag 10A, a caregiver 12 wearing a RTLS tag 12A, a medical device 40 having an attached RTLS tag 40A, and a medication 42 having an attached RTLS tag 42A. This physical space 22 may be a fixed location, such as the interior of a hospital room, or may be a dynamic area surrounding a specific device. For example, a physical space 22 may be defined as centered on the current location of medical device 40, wherein the defined physical space 22 moves with the medical device 40. The medical device 40 may be any device used to diagnose or treat the patient 10 that is also within the defined physical space 22, such as an electrocardiogram (EKG) measurement system, a ventilator, or a simple ear thermometer, as well as an IV pump 14 as shown in the previous figures. The medication 42, presented in the earlier examples as a medical fluid, may be any type of medication including oral solids, ointments, or a gas such as oxygen. A RTLS tag present within defined physical space 22 communicates wirelessly with the RTLS system 44 such that the RTLS system 44 determines that the object having an attached RTLS tag, wherein the RTLS tag has been previously associated with the object, is within the defined physical space 22. The RTLS system 44 communicates with server 46 over a data link 50 such as an Ethernet network. Server 46 is also connected, in this example directly to medical device 40 over a data link 52, which may be the same Ethernet network as data link 50 or a separate wired or wireless network or direct connection allowing server 46 to communicate with medical device 40. Server 46 can, for example, download operational parameters from database 48 to medical device 40 and receive information from medical device 40 regarding caregivers that are in proximity to medical device 40 when certain actions or events occurred. Server 46 is also connected to other systems through an internal and/or external network shown as a "cloud" 99. The other systems may include the hospital's Admit/Discharge/Transfer (ADT) system, a MAR system, a billing system, and portable devices carried by the doctors or nurses. The connection of the RTLS system 44 to the server 46 may be over the Internet or other networks, for example.

Figure 7:
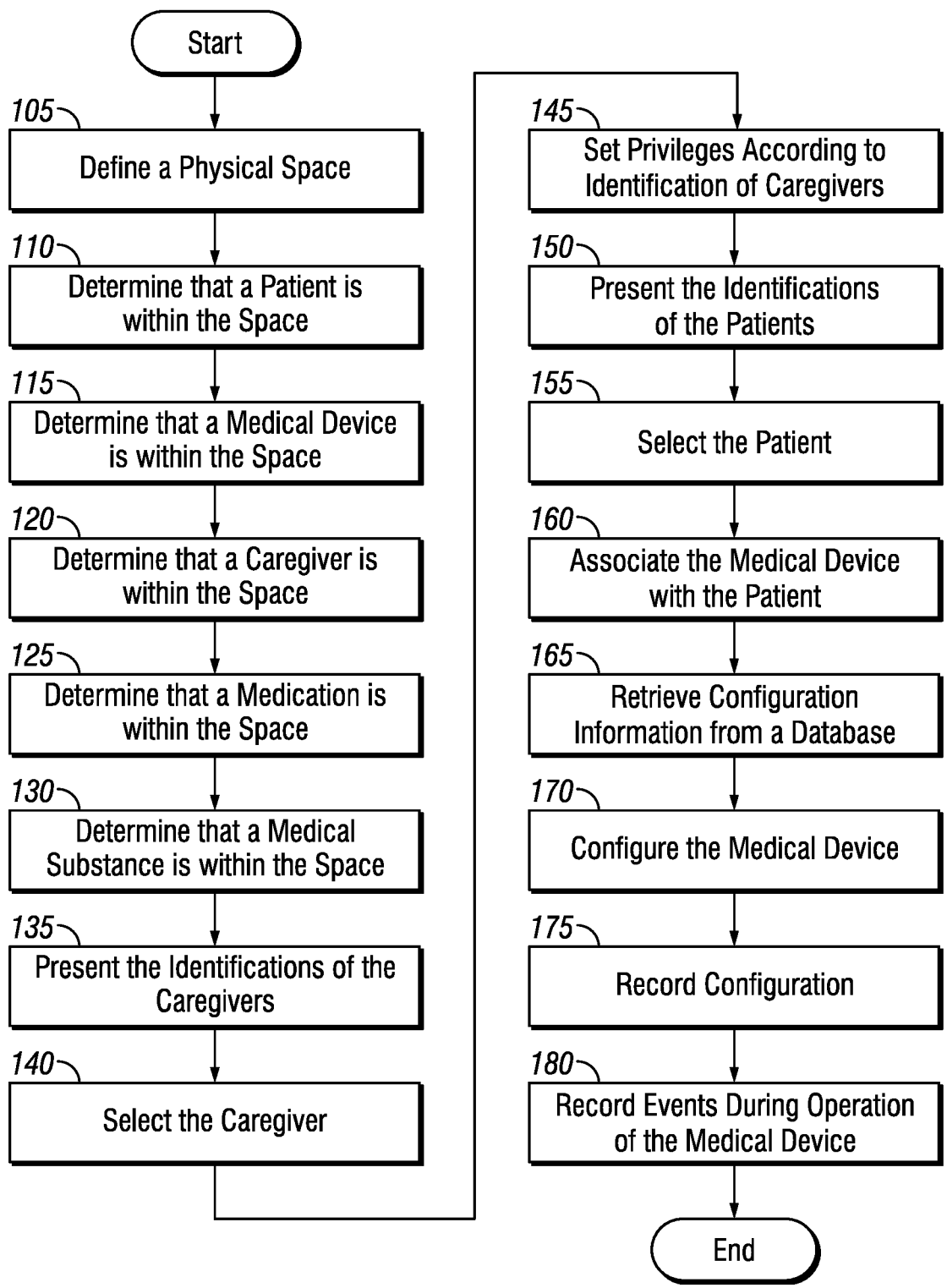
FIG. 7 is a flowchart depicting an exemplary process of associating elements within a defined physical space according to certain aspects of the disclosure.

FIG. 7 is a flowchart depicting an exemplary process of associating elements within a defined physical space according to certain aspects of the disclosure. The process starts in step 105 wherein a physical space is defined. This physical space may be a fixed area or may be a dynamic area linked to an object such as a medical device. Once a physical space is defined, the process proceeds to determine whether one or more of a patient, a medical device, a caregiver, or a medication or medical substance is present within the defined physical space in steps 110, 115, 120, 125, and 130. If multiple caregivers are present within the defined physical space and it is necessary to identify the specific caregiver, for example, when the hospital protocol requires the identification of the individual performing a specific action or as part of a medication administration record, a list of the caregivers located within the defined physical space is presented on, for example, a display of the medical device, a computer terminal located in the room, or a portable device carried by one of the caregivers in step 135. The name of the specific individual can be selected in step 140 by one of the caregivers using the same device that displays the list. In step 145, the privileges associated with all of the caregivers that are present within the defined physical space are retrieved and the medical device is configured to accept input based on the highest privileges of any of the caregivers that are present within the defined physical space. In certain embodiments, the caregiver wishing to configure the medical device must identify himself or herself such as by entering a password whereupon the medical device is configured to accept input based on the privileges of that logged-in caregiver. If multiple patients are present within the defined physical space and it is necessary to identify the specific patient, for example when a medication is to be administered, then a list of patients within the defined physical space is presented (on the same device as used in step 135) in step 150 and the patient is selected by one of the caregivers in step 155. Other similar sets of steps (not shown) are used to identify a specific medical device when multiple medical devices are present within the defined physical space and to identify a specific medication when multiple medications are present within the defined physical space. Once a medical device and a specific patient have been identified, the process proceeds to step 160 wherein the medical device is associated with the patient.

Once the medical device is associated with the patient in step 160, configuration information is retrieved from the database in step 165, wherein the configuration information is associated with at least one of the medication and the medical device that have been determined to be within the defined physical space. In certain embodiments this configuration information includes the operating parameters for the medical device which are downloaded into the medical device directly. In step 170, the caregiver configures the medical device including physical configuration such as connecting an IV set to a source of medical fluid and to the patient and to the medical device as well as adjusting operating parameters of the medical device. In step 175, the configuration and settings and the identification of all of the caregivers that have been determined to be within the defined physical space are recorded in the patient's MAR. In step 180, the medical device is activated and the administration of the medication is initiated. The process stays in step 180 for the duration of the administration of medication and the system records a specified list of events and actions along with the identification of caregivers that are determined to be within the defined physical space at the time the events occur. When the administration of the medication is complete, the process ends.

In summary, the disclosed method and system of associating one or more of a patient, a medical device, a caregiver, and a medication or medical substance provides increased patient safety as well as reducing the workload of the caregiver by implementing configuration changes or documentation that otherwise would be manually accomplished. The automatic association of a patient with a medication when the medication is brought into a defined physical space around the patient and enables the automatic verification that this is the right patient, the right medication, and the right time, covering three of the "five rights" of medication administration. Automatic association of a medical device, such as an IV pump, with a patient facilitates the verification that this is the right route of administration and enables the automatic download of the operating parameters for the medical device, ensuring that the right dose is administered, addressing the remaining two of the "five rights." The automatic association of the caregiver with the medical device enables the automatic logging of events along with the identification of the caregivers that are present, thus reducing the workload of the caregivers. Furthermore, the automatic logging provides the facility with greater data for analysis and improved record-keeping and documentation of actual patient care.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An infusion device configured to:
    automatically determine that the infusion device moved within a physical area associated with a patient, without receiving an input at the infusion device identifying the patient, based on a detection by one or more receiving devices associated with the infusion device of one or more wireless transmitter signals associated with the patient;
    without first identifying the patient to the infusion device, receive an indication of an operation initiated at the infusion device, and
    automatically display on a display screen associated with the infusion device, based on determining the infusion device moved within the physical area associated with the patient and receiving the indication of the operation, an indication of the patient and an electronic list of procedures or prescriptions associated with the patient;

receive, at the infusion device, a selection from the electronic list; and automatically download, based on the selection, from a remote computing device to the infusion device, operating parameters associated with the selection and the patient.

2. The infusion device of claim 1, further configured to:
provide a patient identifier of the patient to the remote computing device; and
receive the electronic list of procedures or prescriptions from the remote computing device after providing the patient identifier and before the electronic list is displayed.

3. The infusion device of claim 1, further configured to:
automatically associate the infusion device with the patient based on determining that the infusion device moved within the physical area associated with the patient.

4. The infusion device of claim 1, further configured to:
automatically identify one or more caregivers within the physical area associated with the infusion device without receiving a logon to the infusion device from the one or more caregivers based on a detection by one or more receiving devices associated with the infusion device of the one or more caregivers within the physical area associated with the infusion device;

authorize use of the infusion device, without further user intervention, based on the indication and detecting that the one or more caregivers are within the physical area associated with the infusion device; and automatically record, based on authorizing use of the infusion device, an association between the infusion device and the one or more caregivers detected within the physical area at a time of the infusion device is used, without receiving a logon of the one or more caregivers at the infusion device.

5. The infusion device of claim 4, wherein a plurality of caregivers are identified in the physical area, and wherein the infusion device is further configured to:
authorize an adjustment to one or more operating parameters of the infusion device according to the highest privileges of the plurality of caregivers identified within the physical area at a time the infusion device is used.

6. The infusion device of claim 5, wherein the infusion device is further configured to:
provide, for display on the display screen associated with the infusion device, a listing of the one or more caregivers detected by the one or more receiving devices; and
receive a selection of a respective caregiver of the one or more caregivers;
receive the adjustment to the one or more operating parameters; and
record the respective caregiver as a caregiver who performed the adjustment.

7. The infusion device of claim 1, wherein the infusion device is further configured to:
identify a medication within the physical area associated with the infusion device based on a wireless transmitter associated with the medication being detected by the one or more receiving devices; and automatically program, by the remote computing device, based on identifying the medication within the physical area, the infusion device with one or more operating parameters associated with administering the medication.

8. The infusion device of claim 7, wherein the infusion device is further configured to:
automatically identify, by the one or more receiving devices, a first patient and a second patient within the physical area associated with the infusion device;
receive parameters for an administration of a medication;
determining that there is a prescription for the medication for the first patient but not the second patient;
automatically associate the infusion device with the first patient based on determining that there is a prescription for the medication for the first patient but not the second patient.

9. The infusion device of claim 1, wherein physical area moves with the infusion device.

10. The infusion device of claim 1, wherein the infusion device is further configured to:
identify a plurality of patients within the physical area associated with the infusion device based on respective wireless transmitters associated with the plurality of patients being detected by the one or more receiving devices;
provide, for display on a display screen associated with the infusion device, a listing of the plurality of patients detected by the one or more receiving devices, before authorizing an administration of a medication by the infusion device;
receive, from the listing, a selection of a respective patient;
associate the respective patient with the infusion device; and
confirm that the medication has been ordered for the selected patient before authorizing performance of the administration of the medication.

11. A computer-implemented method comprising, under control of one or more electronic devices:
automatically determining that an infusion device moved within a physical area associated with a patient, without receiving an input at the infusion device identifying the patient, based on a detection by one or more receiving devices associated with the infusion device of one or more wireless transmitter signals associated with the patient;
without first identifying the patient to the infusion device, receiving an indication of an operation initiated at the infusion device, and
automatically displaying on a display screen associated with the infusion device, based on determining the infusion device moved within the physical area associated with the patient and receiving the indication of the operation, an indication of the patient and an electronic list of procedures or prescriptions associated with the patient;
receiving, at the infusion device, a selection from the electronic list; and
automatically downloading, based on the selection, from a remote computing device to the infusion device, operating parameters associated with the selection and the patient.

12. The computer-implemented method of claim 11, further configured to:
providing a patient identifier of the patient to the remote computing device; and receiving the electronic list of procedures or prescriptions from the remote computing device after providing the patient identifier and before the electronic list is displayed.

13. The infusion device of claim 11, further configured to:
automatically associating the infusion device with the patient based on determining that the infusion device moved within the physical area associated with the patient.

14. The computer-implemented method of claim 11, further configured to:
automatically identify one or more caregivers within the physical area associated with the infusion device without receiving a logon to the infusion device from the one or more caregivers based on a detection by one or more receiving devices associated with the infusion device of the one or more caregivers within the physical area associated with the infusion device;
authorize use of the infusion device, without further user intervention, based on the indication and detecting that the one or more caregivers are within the physical area associated with the infusion device; and
automatically record, based on authorizing use of the infusion device, an association between the infusion device and the one or more caregivers detected within the physical area at a time of the infusion device is used, without receiving a logon of the one or more caregivers at the infusion device.

15. The computer-implemented method of claim 14, wherein a plurality of caregivers are identified in the physical area, the method further comprising:
authorizing an adjustment to one or more operating parameters of the infusion device according to the highest privileges of the plurality of caregivers identified within the physical area at a time the infusion device is used.

16. The computer-implemented method of claim 15, further comprising:
providing, for display on the display screen associated with the infusion device, a listing of the one or more caregivers detected by the one or more receiving devices; and
receiving a selection of a respective caregiver of the one or more caregivers;
receiving the adjustment to the one or more operating parameters; and
recording the respective caregiver as a caregiver who performed the adjustment.

17. The computer-implemented method of claim 11, further comprising:
identifying a medication within the physical area associated with the infusion device based on a wireless transmitter associated with the medication being detected by the one or more receiving devices; and
automatically programming, by the remote computing device, based on identifying the medication within the physical area, the infusion device with one or more operating parameters associated with administering the medication.

18. The computer-implemented method of claim 17, further comprising:
automatically identifying, by the one or more receiving devices, a first patient and a second patient within the physical area associated with the infusion device;
receiving parameters for an administration of a medication;
determining that there is a prescription for the medication for the first patient but not the second patient;
automatically associating the infusion device with the first patient based on determining that there is a prescription for the medication for the first patient but not the second patient.

19. The infusion device of claim 11, wherein the infusion device is further configured to:
identifying a plurality of patients within the physical area associated with the infusion device based on respective wireless transmitters associated with the plurality of patients being detected by the one or more receiving devices;
providing, for display on a display screen associated with the infusion device, a listing of the plurality of patients detected by the one or more receiving devices, before authorizing an administration of a medication by the infusion device;
receiving, from the listing, a selection of a respective patient;
associating the respective patient with the infusion device; and
confirming that the medication has been ordered for the selected patient before authorizing performance of the administration of the medication.

20. A non-transitory machine-readable memory device having instructions stored thereon that, when executed, cause one or more electronic devices to perform operations comprising:
automatically determining that an infusion device moved within a physical area associated with a patient, without receiving an input at the infusion device identifying the patient, based on a detection by one or more receiving devices associated with the infusion device of one or more wireless transmitter signals associated with the patient;
without first identifying the patient to the infusion device, receiving an indication of an operation initiated at the infusion device, and
automatically displaying on a display screen associated with the infusion device, based on determining the infusion device moved within the physical area associated with the patient and receiving the indication of the operation, an indication of the patient and an electronic list of procedures or prescriptions associated with the patient;
receiving, at the infusion device, a selection from the electronic list; and
automatically downloading, based on the selection, from a remote computing device to the infusion device, operating parameters associated with the selection and the patient.

* * * * *